United States Patent
Nam et al.

(10) Patent No.: US 7,033,596 B1
(45) Date of Patent: Apr. 25, 2006

(54) TRANSFORMANT FOR SCREENING OF INHIBITORS FOR HUMAN IMMUNODEFICIENCY VIRUS

(75) Inventors: Hyuk-Jun Nam, Seoul (KR); Sang-Hern Kim, Taejon (KR)

(73) Assignee: Ji-Chang You, Seoul (KR)

( * ) Notice: Subject to any disclaimer, the term of this patent is extended or adjusted under 35 U.S.C. 154(b) by 387 days.

(21) Appl. No.: 10/009,118

(22) PCT Filed: Oct. 18, 2000

(86) PCT No.: PCT/KR00/01173

§ 371 (c)(1), (2), (4) Date: Dec. 6, 2001

(87) PCT Pub. No.: WO01/77312

PCT Pub. Date: Oct. 18, 2001

(30) Foreign Application Priority Data

Apr. 8, 2000 (KR) .......................... 2000-0018489

(51) Int. Cl.
*A61K 39/21* (2006.01)

(52) U.S. Cl. ................................ 424/208.1; 424/188.1

(58) Field of Classification Search ............. 424/188.1, 424/208.1; 435/69.1, 476

See application file for complete search history.

(56) References Cited

OTHER PUBLICATIONS

Bacharach, E., and S. P. Goff, 1998, "Binding of the Human Immunodeficiency Virus Type 1 Gag Protein to the Viral RNA Encapsidation Signal in the Yeast Three-Hybrid System", J. Virol. 72(8):6944-6949.*
Strair, R. K., et al., 1993. "Recombinant Retroviral Systems for the Analysis of Drugs Resistant HIV", Nuc. Acids Res. 21(20):4836-4842.*
"HIV Nucleocapsid Protein, Expression in *Escherichia coli*, Purification, and Characterization," J.C. You et al., *J. Biol. Chem.*, Aug. 5, 1993, 268(22): pp 16519-16527.
"Recombinant retroviral systems for the analysis of drug resistant HIV," R.K. Stair et al., *Nucieic Acids Res.* Oct. 1993, 21(20) pp 4836-4842.
"Beta-Galactosidase containing a human immunodeficiency virus protease cleavage site is cleaved and inactivated by human immunodeficiency virus protease," E.Z. Baum et al., *Proc Natl Acad Sci USA*, Dec. 1990, 87(24), pp 10023-10027.

* cited by examiner

*Primary Examiner*—Jeffrey S. Parkin
(74) *Attorney, Agent, or Firm*—Darby & Darby (57) ABSTRACT

A microorganism cotransformed with a gene expressing HIV nucleocapsid protein and a plasmid vector containing HIV ψ gene and β-galactosidase reporter gene, and a method for screening HIV inhibitors employing the transformant. The invented method comprising the steps of culturing the transformant, treating it with putative compounds or compositions of HIV inhibitors, and measuring the degree of change in β-galactosidase expression in the culture, can be practically applied in screening HIV packaging inhibitors by which the interaction between HIV nucleocapsid and HIV ψ sequence is blocked.

14 Claims, 5 Drawing Sheets

TRANSFORMANT FOR SCREENING OF INHIBITORS FOR HUMAN IMMUNODEFICIENCY VIRUS

This application is a national stage filing under 35 U.S.C. § 371 of International Application No. PCT/KR00/01173, filed Oct. 18, 2000, the entire contents of which are incorporated herein in its entirety.

BACKGROUND OF THE INVENTION

1. Field of the Invention

The present invention relates to a transformant for screening of human immunodeficiency virus("HIV") inhibitors, more particularly, to a transformant cotransformed with a plasmid expressing HIV nucleocapsid protein and a plasmid containing HIV psi(ψ) nucleotide sequence and β-galactosidase reporter gene, and a method for screening of HIV inhibitors by employing the said transformant.

2. Background of the Invention

HIV, a pathogen causing the aquired immunodeficiency syndrome ("AIDS"), selectively infects crucial immune cells called CD4+ T helper cells and replicates inside the cells. Infection of HIV leads to the lysis of CD4+ T cells resulting from an interaction between viral env glycoprotein and plasma membrane of target cell and a subsequent reproduction of virus particles. Also, the binding of soluble gp120 to CD4+ molecules onto uninfected T cells block interactions of CD4+ T cells with other immune cells. In addition to depleting CD4+ T cells, impaired are function of cytotoxic T cells expressing CD8+, antibody-dependent cytotoxicity, maturation of CD4+ T cells in thymus, interaction between CD4+ cells and class II MHC on antigen presenting cells, and function of macrophages and natural killer cells. Thus, human immune system is gradually deteriorated after HIV infection.

Until now, drugs suppressing HIV replication have been developed, which include reverse transcriptase inhibitors such as AZT(azidothymidine) and ddI(dideoxyinosine), and protease inhibitors. Recently, the researches to develop DNA vaccines employing nucleotide sequence encoding HIV proteins (see: Hinkula J. et al., Vaccine, 15:874–878, 1997; Calarota et al., Lancet, 351:1320–1325, 1998), and live-attenuated HIV vaccines made by deleting the HIV nef gene are being undertaken (see: Kestler and Jeang, Science, 270:1219–1222, 1995; Chakrabarti et al., Proc. Natl. Acad. Sci., USA, 93:9810–9815, 1996).

Since the said drugs are not able to remove the provirus of HIV of which DNA is inserted into the host immune cell chromosome or not able to selectively remove host immune cells containing the provirus, it cannot be excluded that HIV variants arisen by genetic mutation acquire drug resistance or HIV revertants arisen by recombination of attenuated virus vaccine acquire characteristics of pathogenic HIV (see: Berkhout et al., J. Virol., 73:1138–1145, 1999). Furthermore, it has been found that HIV requires not only CD4+ molecule as the receptor on the surface of host cells, but also coreceptors such as 'T-cell-line-tropic' CXCR4/fusin coreceptor or 'macrophage-tropic' CCR5 coreceptor for its binding and gaining entry of HIV into host cells (see: Feng et al., Science, 272:872–877, 1996). Thus, one approach for drug therapy is to target these coreceptors in an attempt to inhibit binding of virus onto the host cells. Since the normal function of these coreceptors is to bind 'chemokines (chemotactic cytokines)' which plays a role in inflammation reaction, serious side effects may be anticipated (see: Murphy, P. M., Ann. Rev. Immunol., 12:593–633, 1994). In view of above situation, there is a need to develop a novel class of HIV inhibitors which do not affect host immunity or physiological activity relating to receptors, and one approach for such drug therapy is to target HIV specific factors required for virus assembly.

When HIV virus particle is assembled, its genomic RNA is selectively packaged into a virion. It is well known that a specific interaction between the region of nucleocapsid (NC) protein and the viral packaging sequence (encapsidation signal), psi(ψ), allows selective packaging of viral genomic RNA. Psi(ψ), located between long terminal repeat(LTR) of 5'-terminal of genomic RNA and gag gene which encodes precursor poly protein (matrix-capsid-nucleocapsid), has 4 stem-loop structures. However, the screening of compounds or compositions which inhibit the specific viral interaction required for packaging is difficult due to the lack of an easy and efficient assay system for such screening.

Under the circumstances, there are strong reasons for exploring and developing a model system which can be used to detect the specific interaction between HIV NC protein and HIV psi(ψ) sequence as in in vivo, for screening of inhibitors against HIV packaging.

SUMMARY OF THE INVENTION

The present inventors have made an effort to develop a simple and effective method for detecting the specific interaction between HIV NC protein and HIV psi(ψ) sequence in vivo to screen HIV packaging inhibitors, thus, prepared transformants cotransformed with a plasmid expressing HIV NC protein and a plasmid containing HIV psi(ψ) sequence and β-galactosidase reporter gene, and found that HIV inhibitors can be conveniently screened by employing the said transformant on the basis of the expression level change of β-galactosidase.

A primary object of the invention is, therefore, to provide a transformant cotransformed with a plasmid expressing HIV nucleocapsid protein, and a plasmid containing HIV psi (ψ) sequence and β-galactosidase reporter gene.

The other object of the invention is to provide a method for screening HIV packaging inhibitors employing the said transformant.

BRIEF DESCRIPTION OF THE DRAWINGS

The above, the other objects and features of the invention will become apparent from the following descriptions given in conjunction with the accompanying drawings, in which.

DETAILED DESCRIPTION OF THE INVENTION

The invented transformant employed for screening of HIV packaging inhibitors is prepared by cotransforming a plasmid pJC1 expressing HIV NC protein and a plasmid pNH1Psi(SL1234) containing HIV psi(ψ) gene and β-galactosidase reporter gene.

The process for preparing the transformant for screening of HIV inhibitors is further illustrated in more detail.

Figure 1A:
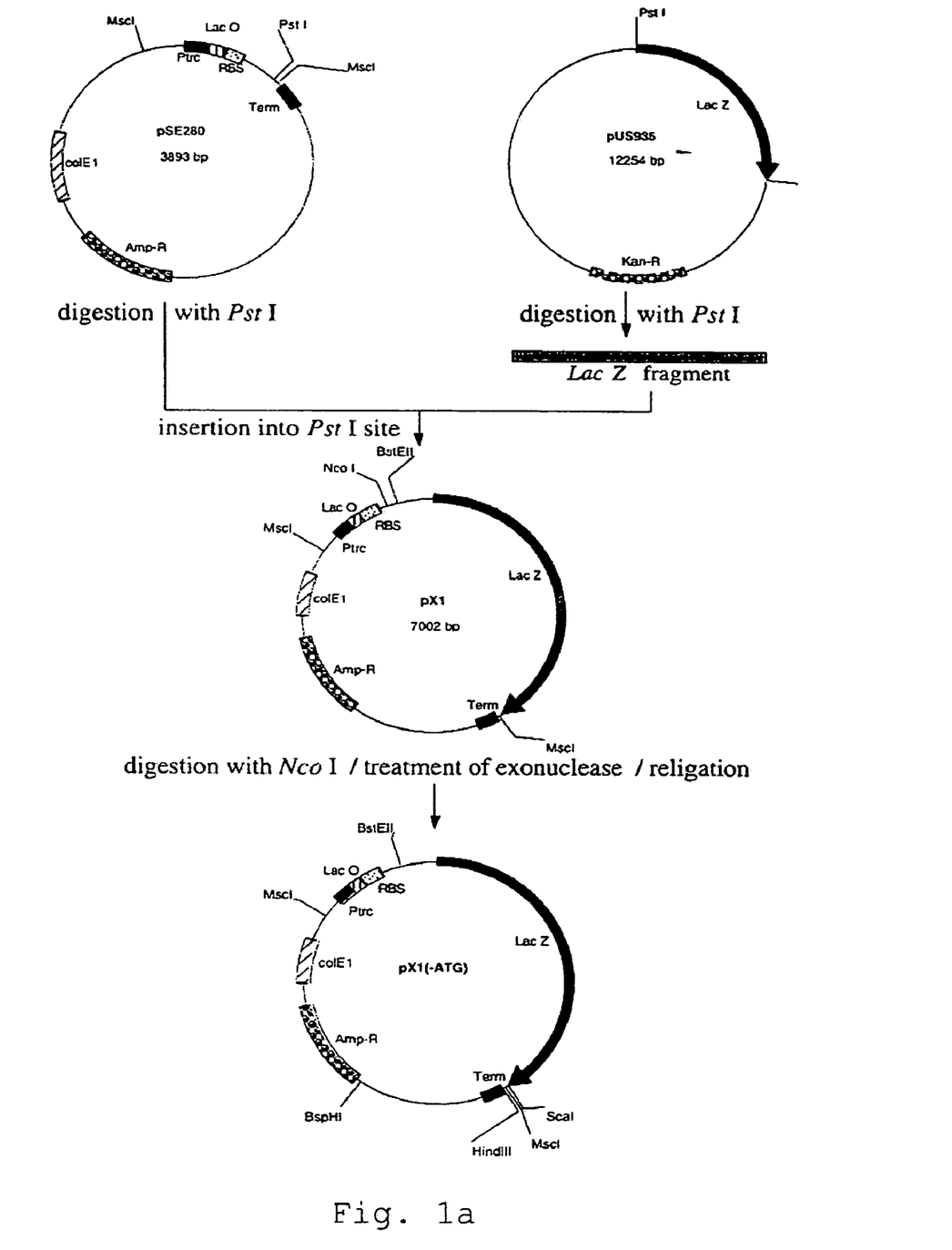
FIG. 1a is a schematic representation of construction strategy of pX1(-ATG).
Figure 1B:
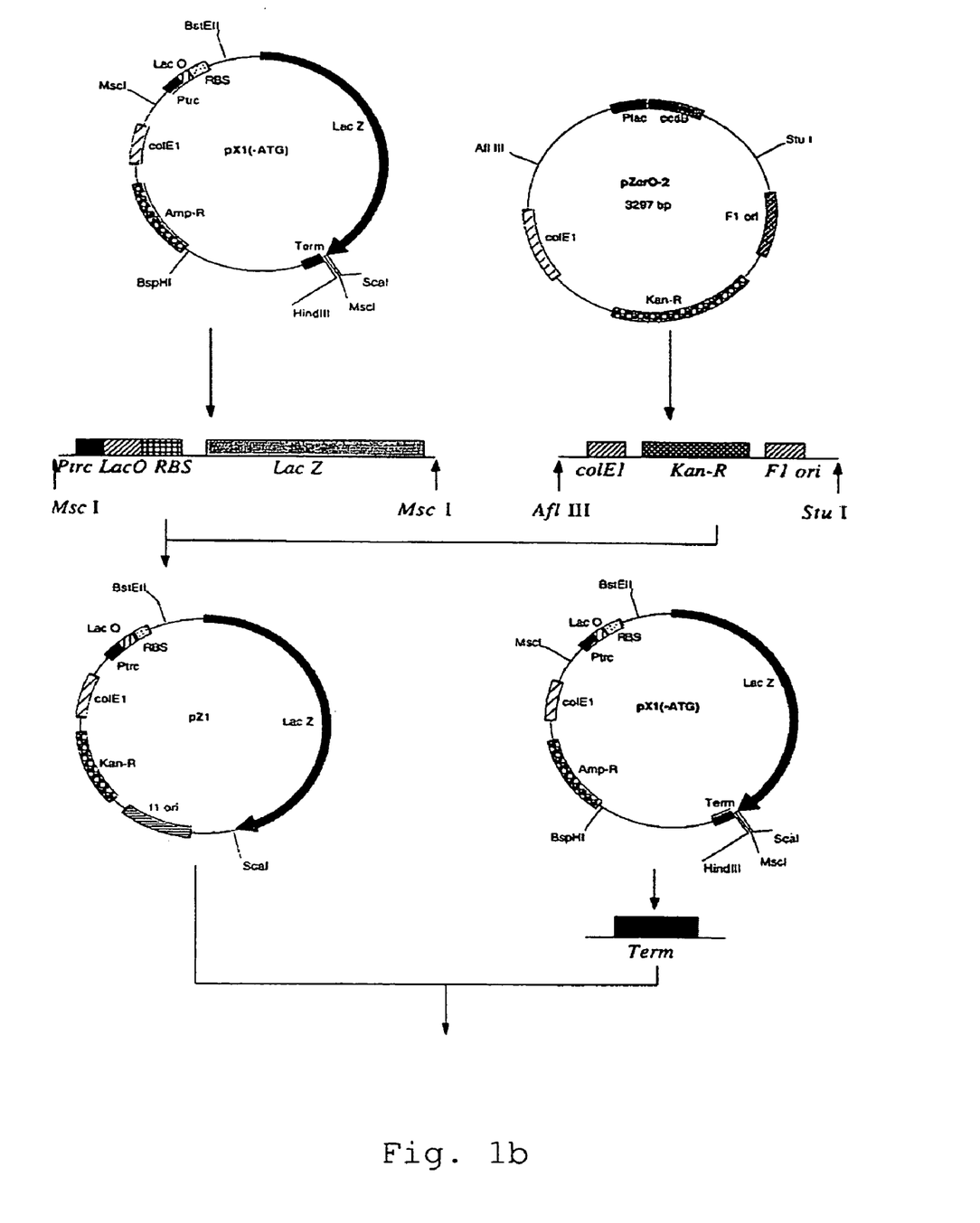
FIG. 1b is a schematic representation of construction strategy of pNH1.
Figure 1C:
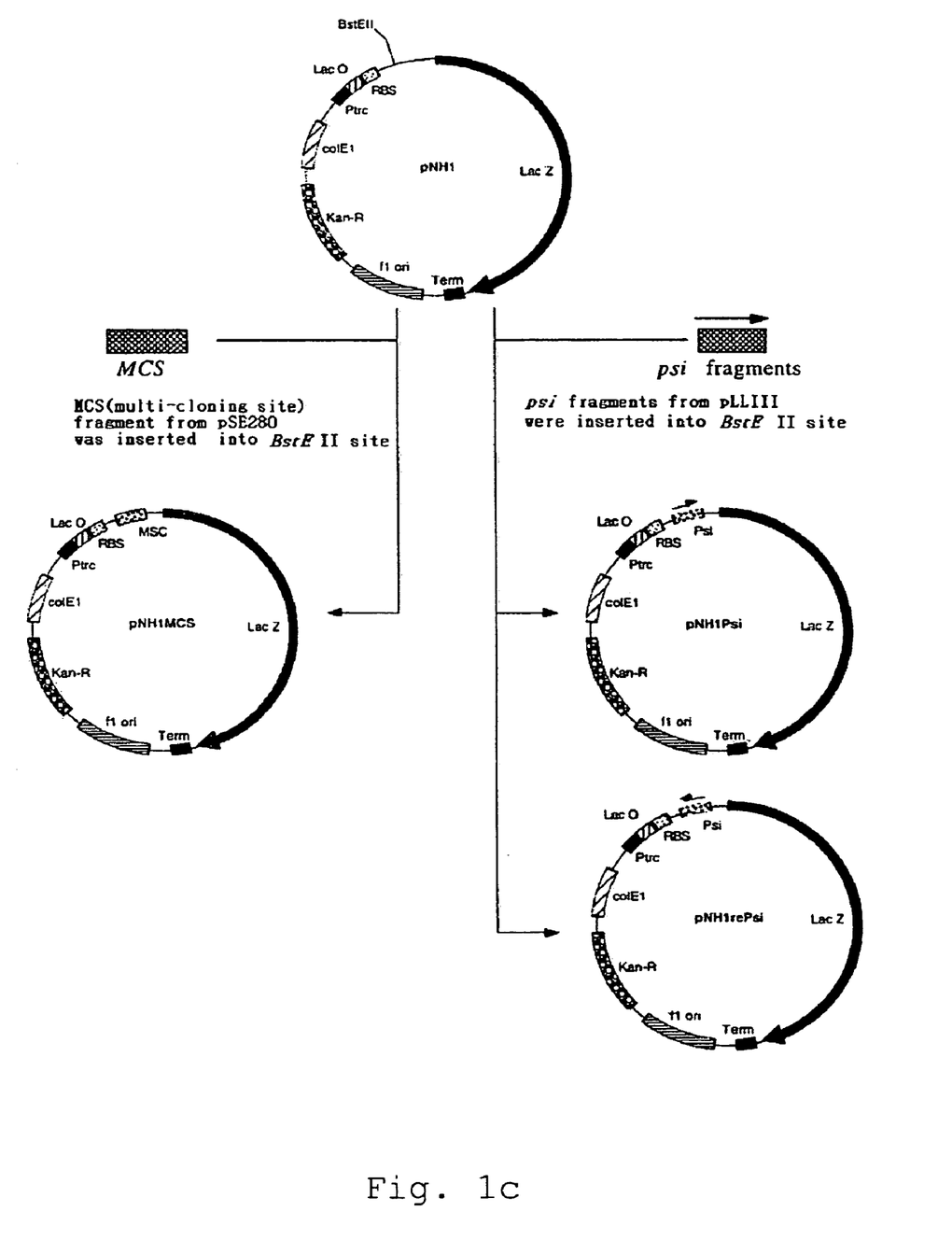
FIG. 1c is a schematic representation of construction strategy of pNH1Psi or pNH1rePsi.

The transformant was prepared by cotransforming with pJC1 expressing HIV NC protein and pNH1Psi(SL1234) containing HIV psi(ψ) gene and β-galactosidase reporter gene: pX1(–ATG) was constructed by removing ATG from pX1 plasmid which was made by inserting lacZ gene fragment into pSE280. And then, pZ1 was obtained by substituting ampicillin resistance gene of pX1(–ATG) with the AflIII-StuI fragment containing kanamycin resistance gene. pNH1 containing lacZ gene was constructed by inserting HindIII-BspH1 fragment containing rrnB T1T2 terminator from pX1(–ATG) into pZ1. pNH1Psi(SL1234) containing lacZ gene which is flanked by HIV psi(ψ) nucleotide sequence right before the starting codon was constructed by inserting 4 stem-loop structure-containing psi(ψ) fragment from pLLIII into pNH1 constructed above (see: FIG. 1). And then, NC protein-expressing pJC1 vector which is constructed by the present inventors (see: Ji Chang You and Charles S. McHenry, J. Biol. Chem., 268:16519–16527, 1993) and pNH1Psi(SL1234) constructed above are cotransformed into *E. coli*. That is, vectors pJC1 and pNH1Psi (SL1234) are cotransformed into *E. coli* by electroporation, followed by selecting antibiotics resistant transformant in medium containing antibiotics. The transformant was named *E. coli*/pNH1Psi(SL1234), and deposited with an international depository authority, the Korean Culture Center of Microorganisms (KCCM, #361–221 Hongje-1-dong, Seodaemun-gu, Seoul, Republic of Korea), under an accession (deposition) No. KCCM-10194 on Mar. 31, 2000. The transformant prepared above has a characteristic that β-galactosidase reporter gene expression is down regulated due to the interaction of psi(ψ) nucleotide sequence with HIV NC protein, thereby it can be used for screening of HIV packaging inhibitors. For instance, the culture of said transformant is treated with putative compounds or compositions of HIV inhibitors, and then the expression level change of β-galactosidase in culture is determined. Therefore, the transformant of the invention can be used for screening of HIV packaging inhibitors which block the binding of HIV NC protein to HIV psi(ψ) nucleotide sequence.

The present invention is further illustrated in the following examples, which should not be taken to limit the scope of the invention.

EXAMPLE 1

Construction of pNH1(SL1234)

A plasmid containing β-galactosidase reporter gene (SEQ ID NO: 1) was constructed.

EXAMPLE 1-1

Construction of pNH1

LacZ gene fragment obtained by PstI (Boeringer Mannheim, Germany) digestion of pUS935(see: Dellagostin, O. A. et al., Microbiology, 141:1785–1792, 1995) was inserted into pSE280(Invitrogen, U.S.A.) to obtain pX1. In order to prevent translation from starting at ATG which is located upstream of the multicloning site of LacZ fragment, upstream ATG was removed by cutting pX1 with NcoI, mung bean exonuclease (Boehringer Mannheim, Germany) treatment, Klenow enzyme treatment to create blunt end and then ligating to make pX1(–ATG). FIG. 1*a* is a schematic representation of construction strategy of pX1(–ATG). pZ1 was made by substituting ampicillin resistance gene of pX1(–ATG) with a kanamycin resistance gene, that is, by ligating the lacZ gene-containing MscI fragment from pX1 (–ATG) and Kan$^r$ gene-containing AflIII-StuI fragment from pZerO-2(Invitrogen, U.S.A.). Then, pNH1 was made by inserting rrn T1T2 terminator-containing HindIII-BspHI fragment from pX1(–ATG) into the ScaI site of pZ1. FIG. 1*b* is a schematic representation of construction strategy of pNH1.

EXAMPLE 1-2

Construction of pNH1Psi(SL1234)

pLLIII (University of Colorado, Health Sciences Center, Charles S. McHenry), a plasmid containing the 5' long terminal rep eat (LTR) of HIV-1, was digested with SacI and MseI and then treated with Klenow enzyme to obtain a fragment containing HIV psi(ψ) nucleotide sequence (named "SL1234", SEQ ID NO: 2) which contains 4 stem-loop structures.

SL1234 was digested with MaeI and then treated with Klenow fragment to obtain SL12(SEQ ID NO: 3). pNH1Psi (SL1234) or pNH1Psi(SL12) was made by inserting SL1234 or two fragments of SL12 into the BstEII site which is located upstream of lacZ gene in pNH1, respectively. Then, pNH1rePsi(SL1234) or pNH1rePsi(SL12) containing HIV psi(ψ) nucleotide sequence in reverse orientation was made to be used as a control vector. DNA bands of 221 bp for right orientation and 152 bp for reverse orientation were identified by 2% agarose gel electrophoresis.

Primers, U2 and L3 pair or U2 and L4 pair, were used for amplification of SL23(SEQ ID NO: 4) or SL234(SEQ ID NO: 5), respectively, and their nucleotide sequences are as follows.

primer U2 (SEQ ID NO: 6) 5'-GGGGGTGACCTT-TAAAAGCAAGAGGCGAGGG-3' primer L3 (SEQ ID NO: 7) 5'-GGGGGTGACCCTCTC-CTTCTAGCCTCCG-3' primer L4 (SEQ ID NO: 8) 5'-GGGGGTGAC-CGACGCTCTCGCACCCGTCTCT-3'

In order for easier insertion of psi(ψ) fragment into BstEI site in pNH1, BstEII site (boldface) was inserted into the each primer, and DraI site (boldface) was inserted into the primer U2 to identify orientation. Also, point mutation (underlined), T to G, was introduced into primer L4 to prevent translation from starting in the psi(ψ) sequence. PCR was performed in a 100 μl of reaction mixture containing 10 mM Tris-HCl, pH 7.5, 1.5 mM MgCl$_2$, 50 mM KCl, 1 mM dNTP, 10 M of each primer, 1 μg of pLLIII and 2.5 unit of Taq polymerase (Boehringer Mannheim, Germany) with preincubation at 94° C. for 5 min, 30 cycles of denaturation at 94° C. for 1 min, primer annealing at 60° C. for 2 min, and extension at 72° C. for 2 min, and then additional extension at 72° C. for 10 min. For SL23 insertion, DNA bands of 213 bp for right orientation and 146 bp for reversed orientation were identified by 2% agarose gel electrophoresis following digestion of each plasmid with DraI. For SL234 insertion, DNA bands of 234 bp for right orientation and 146 bp for reversed orientation were identified by 2% agarose gel electrophoresis following digestion of each plasmid with DraI.

SL34 fragment obtained by digestion of PCR product, SL234, with RsaI and BstEII, was treated with Klenow fragment, and then inserted into the BstEII site of pNH1 to make pNH1Psi(SL34) and pNH1rePsi(SL34) as a control. DNA bands of 40 bp for right orientation and 56 bp for reversed orientation were identified by 4% agarose gel electrophoresis following double-digestion of each plasmid with BsmAI and XmnI.

In order to use as a negative control, that is, to see whether NC protein or Gag protein can interact with nucleotide sequence which is non-homologous to psi(ψ), pNH1MCS was made by inserting 75 bp MCS (multicloning site) fragment, which has no ATG starting codon, obtained by digestion of pSE280 with MaeI and subsequent Klenow treatment, into the BstEII site of pNH1. DNA band of 229 bp was identified by 2% agarose gel electrophoresis following RsaI digestion. FIG. 1c is a schematic representation of construction strategy of pNH1Psi or pNH1rePsi.

EXAMPLE 2

Expression of HIV NC Protein or HIV Gag Protein

NC protein-expressing plasmid, pJC1, which was made and disclosed by the present inventors (see: Ji Chang You, and Charles S. McHenry, J. Biol. Chem., 268(22):16519–16527, 1993) or Gag protein-expressing plasmid, pTrcHisGag, was transformed into E. coli strain JM109(Promega Co., U.S.A.) by electroporation: to obtain competent cells, overnight culture of JM109 started from single colony was inoculated into 200 ml of fresh LB medium (Luria-Bertani, Difco, U.S.A.) with 1:100 dilution and cultivated to OD 0.5–0.7, and then cells were centrifuged at 4000 g for 10 min., followed by 4 times of washing process which was resuspending cell pellet in cold 10% (v/v) glycerol and centrifugation at 4000 g for 10 min. After being resuspended in 1 ml, 20 μl of competent cells were mixed with 1–100 ng of DNA, transferred to 0.2 cm gap electroporation cuvette, and transformed in E. coli pulser (Bio-Lab, Heracules, Calif., U.S.A.) by applying 2.5 kV electric shock. The transformant was incubated overnight in LB medium containing 100 μg of ampicillin, and then subcultured in fresh LB medium with 1:100 dilution. At the early period of logarithmic phase of growth, 1 mM of isopropyl-β-D-thiogalactopyranoside (IPTG, Roche Diagnostics, Germany) was added and the proteins were induced for 3 hours. The liquid culture of transformant was sampled at each hour and centrifuged at 10,000 g for 1 min. The cell pellet was resuspended in 20 μl of gel loading buffer (50 mM Tris-HCl, pH 6.8, 100 mM dithiothreitol, 2% SDS, 0.1% bromophenol blue and 10% glycerol), and incubated for 5 min at 100° C. to disrupt cell wall. After centrifugation at 10,000 g for 30 min, each supernatant was subject to 15% SDS-PAGE at 120V for 2 hours. The gel was stained in staining solution (0.25% Coomassie Brilliant Blue, 45% methanol and 10% glacial acetic acid) for 20 min and then destained in destaining solution (30% methanol and 10% acetic acid) for 2 hours. Although HIV NC protein (7 kD) band did not appear without IPTG induction, the protein band at 7 kD position was getting thicker after IPTG induction as time went by Also, HIV Gag protein (55 kD) band appeared at about 55 kD position after IPTG induction.

EXAMPLE 3

Cotransformation and Measurement of β-galactosidase expression

In order to measure the effect of interaction between HIV psi(ψ) nucleotide sequence and HIV NC protein or Gag protein on β-galactosidase expression level, pJC1 and each of pNH1Psi plasmids or pTrcHisGag and each of pNH1Psi plasmids were cotransformed into E. coli JM109 by electroporation, respectively. To exclude the possibility of plasmid copy number effect and to confirm the expression of lac repressor, JM109 was cotransformed with pSE380(Invitrogen, U.S.A.) as a control plasmid and each of pNH1Psi plasmids. Each cotransformant was selected on LB agar plate containing 100 μg/ml ampicillin and 40 μg/ml kanamycin.

To measure the expression of β-galactosidase in the cotransformants, β-galactosidase liquid assay was performed for each cotransformant more than 3 times. Each cotransformant was cultured in LB medium overnight, and the culture broth was inoculated into 5 ml of fresh LB medium with 1:10 dilution. At the early stage of logarithmic phase of growth, 1 ml aliquot of culture broth was taken and kept on ice, and then incubation was continued for 3 hours to allow expression of NC protein, Gag protein and β-galactosidase after 1 mM IPTG was added for induction of β-galactosidase. And then, 1 ml aliquot of culture broth was sampled each hour and kept on ice. Cell density was measured at $A_{600}$ with enzyme-linked immunosorbent assay reader (ELISA reader, Dynatech, U.S.A.). For measurement of β-galactosidase activity, 50 g aliquot of each cotransformant culture broth was mixed with 450 μl aliquot of Z buffer (60 mM Na$_2$HPO$_4$ 7H$_2$O, 40 mM NaH$_2$PO$_4$.H$_2$O, 10 mM KCl, 1 mM MgSO$_4$ 7H$_2$O, 50 mM β-mercaptoethanol). And then, cell wall was disrupted by addition of 20 μl of chloroform and 10 μg of 0.1% SDS followed by stirring for 30 seconds and incubating at 28° C. for 5 min. To the cell lysate, 100 μl of o-nitrophenyl-1-thio-β-D-galactopyranoside (ONPG, 4 mg/ml, Sigma, U.S.A.) was added and the mixture was incubated at room temperature until yellow color developed. When yellow color was fully developed, the reaction was stopped by adding 200 μl of 1M Na$_2$CO$_3$, and the mixture was clarified by centrifugation at 10,000 g for 30 min. Optical density (OD) of supernatant was measured at 420 nm and 550 nm. The activity (units) of β-galactosidase was quantitated by following equation:

$$\text{Enzyme unit of } \beta\text{-galactosidase} = 1{,}000 \times (OD_{420} - 1.75 \times OD_{550})/(t \times OD_{600})$$

wherein, t is reaction time (minutes); and, 1.75 is a constant.

Figure 2:
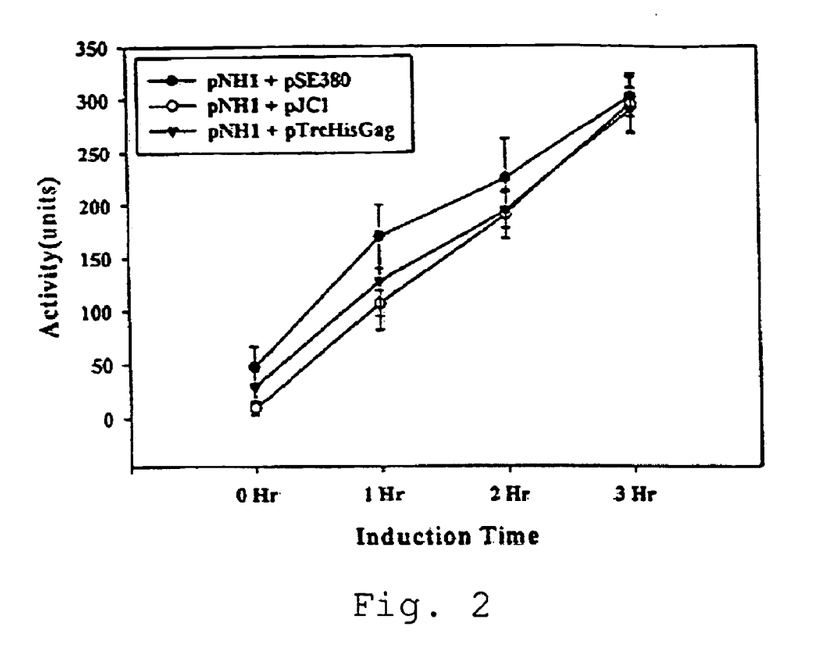
FIG. 2 is a graph showing the expression of β-galactosidase in E. coli JM109 cotransformed with each of pJC1 expressing nucleocapsid protein, or pTrcHisGag expressing Gag protein, or pSE380 as a control plasmid, and pNH1, respectively.

In order to determine if NC protein or Gag protein affect the β-galactosidase expression from the plasmid without psi(ψ) sequence, E. coli JM109 was cotransformed with the precursor plasmid, pNH1(containing lacZ gene, no psi(ψ) sequence) and pJC1(nucleocapsid), pNH1 and pTrcHisGag (Gag protein), or pNH1 and pSE380(control), respectively, and then, β-galactosidase activity was measured as described above. FIG. 2 is a graph showing the expression of β-galactosidase in JM109 cotransformed with each of pJC1 expressing nucleocapsid protein, pTrcHisTag expressing Gag protein, or pSE380 as a control plasmid, and pNH1. As shown in FIG. 2, the level of β-galactosidase expression in cotransformant expressing NC protein or Gag protein was not different from that in cotransformant expressing no other protein (pSE380) after 3 hour-induction of β-galactosidase with IPTG, therefore, it was demonstrated that NC protein or Gag protein had no effect on the expression of β-galactosidase in cotransformants.

Figure 3A:
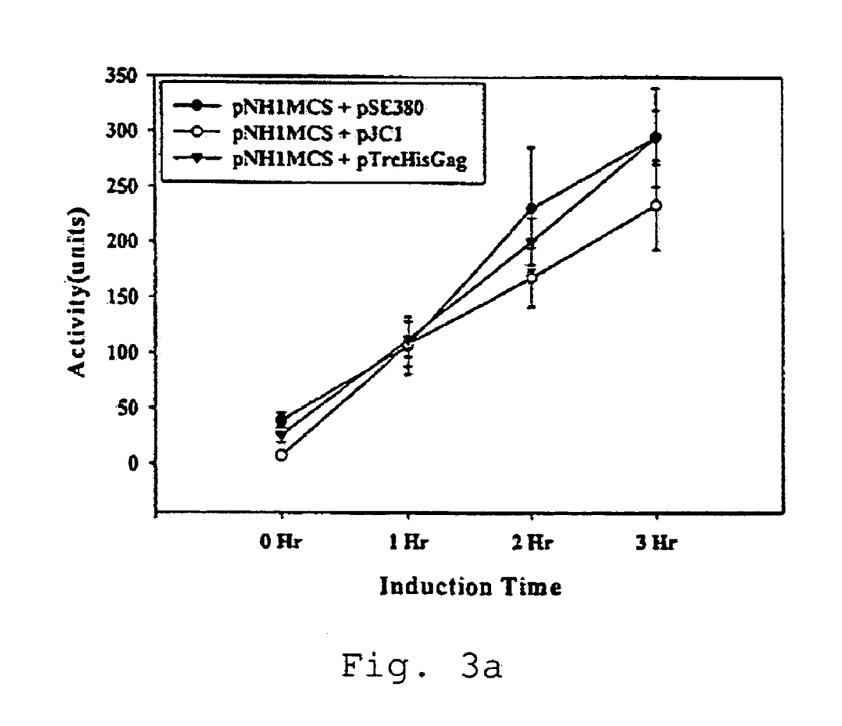
FIG. 3a is a graph showing the effect of interaction between HIV nucleocapsid protein or Gag protein and HIV psi(ψ) sequence on the expression of β-galactosidase after induction with IPTG in E. coli JM109 cotransformed with each of pJC1, pTrcHisGag or pSE380 and pNH1MCS, respectively.
Figure 3B:
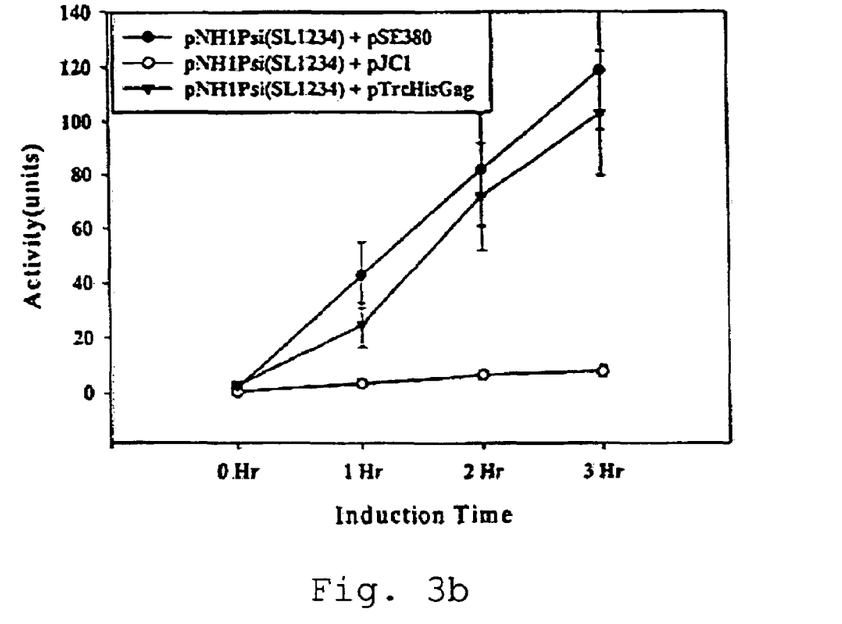
FIG. 3b is a graph showing the effect of specific interaction between HIV nucleocapsid protein or Gag protein and HIV psi(ψ) sequence on the expression of β-galactosidase after induction with IPTG in *E. coli* JM109 cotransformed with each of pJC1, pTrcHisGag or pSE380 and pNH1Psi (SL1234), respectively.

In order to demonstrate the specificity of the interaction between HIV NC protein and HIV psi(ψ) sequence or Gag protein and HIV psi(ψ) sequence, β-galactosidase expression was measured in cotransformants containing each of pSE380, pJC1 or pTrcHisGag and each of pNH1MCS (multiple cloning site, MCS, as a non-homologous sequence to HIV psi(ψ) nucleotide sequence) or pNH1Psi(SL1234, HIV psi(ψ) nucleotide sequence), respectively. FIG. 3a is a graph showing the effect of interaction between HIV nucleocapsid protein or Gag protein and non-homologous sequence to psi(ψ) on the expression of β-galactosidase after induction with IPTG in JM109 cotransformed with each of pJC1, pTrcHisTag or pSE380 and pNH1MCS. FIG. 3b is a graph showing the effect of specific interaction between HIV nucleocapsid protein or Gag protein and homologous psi(ψ) sequence on the expression of β-galactosidase after induction with IPTG in JM109 cotransformed with each of pJC1, pTrcHisGag or pSE380 and pNH1Psi(SL1234), respectively. As shown in FIG. 3a, the level of β-galactosidase in cotransformants containing non-homologous sequence (pNH1MCS) to psi(ψ) and a plasmid expressing NC protein or Gag protein was not different from that in cotransformant containing pHN1MCS and control plasmid, pSE380. Meanwhile, as shown in FIG. 3b, when transformed together with pNH1psi(SL1234), the level of β-galactosidase in cotransformant expressing Gag protein was reduced by 15% compared to that in cotransformant containing control vector, pSE380, moreover, cotransformant expressing NC protein showed more than 90% reduction in β-galactosidase expression compared to the control cotransformant.

Therefore, it was demonstrated that β-galactosidase expression in cotransformant was reduced by HIV NC protein in the presence of HIV psi(ψ) nucleotide sequence and the reduction was caused by a specific interaction between HIV NC protein and HIV psi(ψ) nucleotide sequence.

Figure 4:
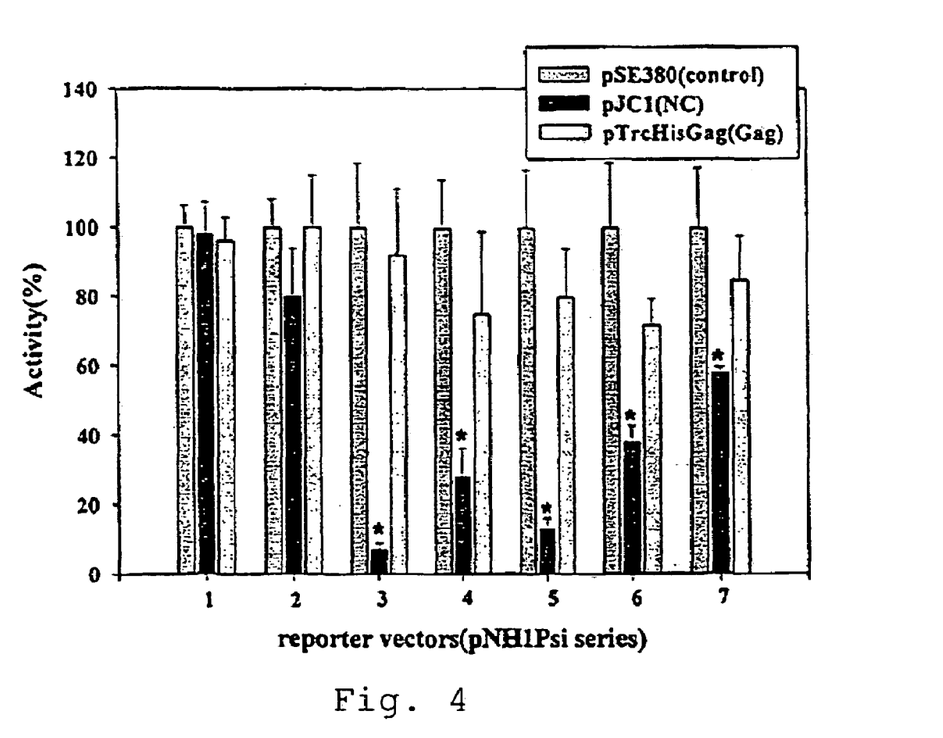
FIG. 4 is a graph showing the effect of specific interaction between HIV nucleocapsid protein or Gag protein and various portions of psi(ψ) sequence on the expression of β-galactosidase in *E. coli* JM109 which is cotransformed with each of pJC1, pTrcHisGag or pSE380 and each of plasmid pNH1Psi(SL1234), pNH1Psi(SL234), pNH1Psi (SL34), pNH1Psi(SL23), or pNH1Psi(SL12) containing psi (ψ) nucleotide sequence, respectively.

In order to identify which portion of psi(ψ) nucleotide sequence is responsible for the specific interaction with NC protein, each of plasmids containing various portions of stem-loop structures of psi (ψ) nucleotide sequence were cotransformed with NC- or Gag-expressing vector into E. coli JM109, respectively, and then β-galactosidase activity of each cotransformant was measured. FIG. 4 is a graph showing the effect of specific interaction between HIV NC protein or Gag protein and portions of psi(ψ) sequence on the expression of β-galactosidase in E. coli JM109 cotransformants. E. coli JM109 was cotransformed with each of pJC1, pTrcHisGag, or pSE380 and each of plasmids containing various portion of stem-loop structures of psi(ψ) nucleotide sequence, pNH1Psi(SL1234), pNH1Psi(SL234), pNH1Psi(SL34), pNH1Psi(SL23), or pNH1Psi(SL12), respectively. In FIG. 4, horizontal axis indicates the cotransformants containing each of pJC1, pTrcHisGag, or pSE380 and each of psi(ψ) structure-containing plasmids (lane 1 is control plasmid, pNH1; lane 2, a plasmid containing non-homologous sequence, pNH1MCS; lane 3, pNH1Psi (SL1234); lane 4, pNH1Psi(SL234); lane 5, pNH1Psi (SL34); lane 6, pNH1Psi(SL23); and, lane 7, pNH1Psi (SL12)), and vertical axis indicates the activity of β-galactosidase. The results were statistically analyzed by Student's test and * indicates $p<0.05$. As shown in FIG. 4, HIV NC protein reduced the expression of lacZ gene more effectively when psi(ψ) sequence is present in cell than HIV Gag protein did. When pNH1Psi(SL1234) containing full length psi(ψ) nucleotide sequence and pJC1 were cotransformed into pJM109, the reduction of lacZ expression was most significant, and the degree of reduction was decreased in the order of SL34, SL234, SL23, and SL12. The sequence of SL4 appears to be more important than other stemp-loop structures for the specific interaction of psi(ψ) sequence with NC protein which resulted in the reduction of lacZ gene expression.

Therefore, these results demonstrated that all of 4 stem-loop structures in psi(ψ) sequence was required for the most significant reduction of β-galactosidase expression, and sequence of SL4 was the most important portion in psi(ψ) sequence for NC protein binding. And, the degree of reduction of lacZ gene expression in pNH1Psi(SL234) and pNH1Psi(SL34) which were point-mutated to avoid translation starting from SL4 area was similar to that in pNH1Psi (SL1234) without point mutation. Thus, the transformant was named as E. coli/pNH1Psi(SL1234), which showed the most significant reduction of β-galactosidase expression by specific interaction of psi(ψ) sequence with NC protein. E. coli/pNH1Psi(SL1234) was deposited with an international depository authority, the Korean Culture Center of Microorganisms (KCCM, #361–221 Hongje-1-dong, Seodaemun-gu, Seoul, Republic of Korea), under an accession (deposition) No. KCCM-10194 on Mar. 31, 2000. The results obtained from the above Examples were summarized in Table 1 below.

TABLE 1

Level of β-galactosidase expression
depending on kinds of reporter vectors

| Reporter Vector | | Enzyme units of β-galactosidase after 3-hour induction | | | | | |
|---|---|---|---|---|---|---|---|
| | | pSE380 (Control) | | pJC1 (expressing NCp7) | | pTrcHisGag (expressing Gag) | |
| pNH1 | — | 302 ± 19* | 100% | 295 ± 28.7 | 98% | 298 ± 20.8 | 96% |
| pNH1MCS | 75 bp | 296 ± 24.5 | 100% | 234 ± 40.5 | 80% | 296 ± 44.5 | 100% |
| pNH1Psi (SL1234) | SL1234 | 119 ± 22 | 100% | 8 ± 2.2 | 6.7% | 103 ± 23 | 86.5% |
| pNH1Psi (SL234) | SL234 | 308 ± 42.5 | 100% | 87 ± 25.5 | 28% | 140 ± 44 | 76% |
| pNH1Psi (SL34) | SL34 | 85 ± 14 | 100% | 11 ± 2.6 | 13% | 68 ± 12 | 80% |
| pNH1Psi (SL23) | SL23 | 298 ± 55.5 | 100% | 112 ± 14 | 38% | 214 ± 22.5 | 72% |
| pNH1rePsi (SL12) | SL12 | 186 ± 32 | 100% | 107 ± 3.5 | 58% | 158 ± 24 | 85% |
| pNH1rePsi (SL1234) | reSL1234 | 87 ± 21 | 100% | 51 ± 10 | 59% | 85 ± 17 | 98% |
| pNH1rePsi (SL234) | reSL234 | 185 ± 37 | 100% | 78 ± 5 | 42% | 140 ± 30.5 | 76% |
| pNH1rePsi (SL34) | reSL34 | 311 ± 29 | 100% | 186 ± | 60% | 307 ± 30 | 99% |
| pNH1rePsi (SL23) | reSL23 | 305 ± 43 | 100% | 131 ± 19 | 43% | 280 ± 18 | 92% |
| PNH1Psi (SL12) | reSL12 | 86 ± 21 | 100% | 64 ± 11 | 75% | 86 ± 19.5 | 100% |

As a result, it is a characteristic of the transformant to be reduced in β-galactosidase reporter gene expression due to the specific interaction between psi(ψ) nucleotide sequence and HIV NC protein. Therefore, the transformant of the invention can be used for screening of HIV packaging inhibitors which block the binding of HIV NC protein to HIV psi(ψ) nucleotide sequence, by treating the culture broth of *E. coli* JM109(KCCM-10194) with putative compounds or compositions of HIV inhibitors and measuring the degree of change in β-galactosidase expression.

As clearly illustrated and demonstrated above, the present invention provides a microorganism cotransformed with a gene expressing HIV nucleocapsid protein and a plasmid vector containing HIV Psi (ψ) gene and β-galactosidase reporter gene, and a method for screening HIV packaging inhibitors employing the said transformant. The invented method comprising the steps of culturing the said transformant, treating it with putative compounds or compositions of HIV inhibitors, and measuring the degree of change in β-galactosidase expression in the culture, can be practically applied in screening HIV packaging inhibitors by which the interaction between HIV nucleocapsid and HIV psi(ψ) sequence is blocked.

What is claimed is:

1. A microorganism cotransformed with a plasmid vector containing a gene expressing the HIV nucleocapsid protein, and a plasmid vector containing the HIV psi (ψ) sequence and a reporter gene located downstream of the HIV psi (ψ) sequence, wherein reporter gene expression is downregulated by the specific binding interaction of the psi sequence with the nucleocapsid protein.

2. The microorganism of claim 1 wherein the plasmid vector containing a gene expressing the HIV nucleocapsid protein is pJC1.

3. The microorganism of claim 1 wherein the HIV psi (ψ) sequence is selected from the group consisting of SL1234 (SEQ ID NO: 2), SL234 (SEQ ID NO: 5), SL23 (SEQ ID NO: 4), and SL12 (SEQ ID NO: 3).

4. A microorganism comprising E. coli JM109 (KCCM-10194) cotransformed with a vector pJC1 expressing the HIV nucleocapsid protein, and a vector pNH1Psi(SL1234) containing the HIV psi(ψ) sequence and β-galactosidase reporter gene (SEQ ID NO: 1) located downstream of the HIV psi(ψ) sequence, wherein β-galactosidase expression is downregulated by the specific binding interaction of the psi sequence with the nucleocapsid protein.

5. A microorganism cotransformed with the vector pJC1 expressing the HIV nucleocapsid protein, and a vector pNH1Psi(SL234) containing the HIV psi (ψ) sequence and β-galactosidase reporter gene (SEQ ID NO: 1) located downstream of the HIV psi(ψ) sequence, wherein β-galactosidase expression is downregulated by the specific binding interaction of the psi sequence with the nucleocapsid protein.

6. A microorganism cotransformed with the vector pJC1 expressing the HIV nucleocapsid protein, and a vector pNH1Psi(SL23) containing the HIV psi (ψ) sequence and β-galactosidase reporter gene (SEQ ID NO: 1) located downstream of the HIV psi(ψ) sequence, wherein β-galactosidase expression is downregulated by the specific binding interaction of the psi sequence with the nucleocapsid protein.

7. A microorganism cotransformed with the vector pJC1 expressing the HIV nucleocapsid protein, and a vector pNH1Psi(SL12) containing the HIV psi(ψ) sequence and β-galactosidase reporter gene (SEQ ID NO: 1) located downstream of the HIV psi(ψ) sequence, wherein β-galactosidase expression is downregulated by the specific binding interaction of the psi sequence with the nucleocapsid protein.

8. A microorganism transformed with a vector pNH1Psi (SL1234) containing the HIV psi (ψ) gene and β-galactosidase reporter sequence (SEQ ID NO: 1) located downstream of the HIV psi(ψ) sequence, wherein β-galactosidase expression is down-regulated by the specific binding interaction of the psi sequence with the nucleocapsid protein.

9. A microorganism wherein both a plasmid vector containing a gene coding for the HIV nucleocapsid protein and a plasmid vector containing the HIV psi (ψ) sequence and β-galactosidase reporter gene (SEQ ID NO: 1) located downstream of the HIV psi(ψ) sequence are integrated into a chromosome, wherein β-galactosidase expression is downregulated by the specific binding interaction of the psi sequence with the nucleocapsid protein.

10. A method of screening for HIV packaging inhibitors which comprises the steps of:

(i) culturing the cotransformed microorganism of claim 1;

(ii) treating the said cotransformed microorganism with putative compounds or compositions of HIV inhibitors; and, (iii) measuring the degree of change in reporter gene expression in the culture, wherein an increase in reporter gene expression in the presence of the compound or composition compared to reporter gene expression in the absence of the compound or composition indicates the compound or composition inhibits the specific binding interaction between the HIV nucleocapsid protein and the psi sequence.

11. The method of claim 10 wherein the cotransformed microorganism is *E. coli* JM109 (KCCM-10194).

12. The microorganism of claim 1, wherein the reporter gene is β-galactosidase.

13. The microorganism of claim 12 wherein the β-galactosidase reporter gene is SEQ ID NO: 1.

14. The microorganism of claim 13 wherein the plasmid vector containing the HIV psi(ψ) sequence and β-galactosidase reporter gene is selected from the group consisting of pNH1Psi(SL1234), pNH1Psi(SL234), pNH1Psi(SL23), pNH1Psi(SL12), and pNH1Psi(SL34).

* * * * *

SEQUENCE LISTING

<160> NUMBER OF SEQ ID NOS: 8

<210> SEQ ID NO 1
<211> LENGTH: 3279
<212> TYPE: DNA
<213> ORGANISM: Artificial Sequence
<220> FEATURE:
<223> OTHER INFORMATION: beta-galactosidase gene

<400> SEQUENCE: 1

```
atgggacgtc gacctgaggt aattataacc cgggccctat atatggatcc aattgcaatg      60
atcatcatga cagatctgcg cgcgatcgat atcagcgctt taaatttgcg catgctagct     120
atagttctag aggtaccggt tgttaacgtt agccggctac gtatactccg gaatattaat     180
aggcctagga tgcatatggc ggccgcctgc aggtcgactc tagaggatcc cgtcgtttta     240
caacgtcgtg actgggaaaa ccctggcgtt acccaactta atcgccttgc agcacatccc     300
cctttcgcca gctggcgtaa tagcgaagag gcccgcaccg atcgcccttc ccaacagttg     360
```

-continued

```
cgcagcctga atggcgaatg gcgctttgcc tggtttccgg caccagaagc ggtgccggaa      420
agctggctgg agtgcgatct tcctgaggcc gatactgtcg tcgtcccctc aaactggcag      480
atgcacggtt acgatgcgcc catctacacc aacgtaacct atcccattac ggtcaatccg      540
ccgtttgttc ccacggagaa tccgacgggt tgttactcgc tcacatttaa tgttgatgaa      600
agctggctac aggaaggcca gacgcgaatt attttttgatg cgttaactc ggcgtttcat      660 ctgtggtgca acgggcgctg gtcggttac ggccaggaca gtcgtttgcc gtctgaattt      720
gacctgagcg cattttttacg cgccggagaa accgcctcg cggtgatggt gctgcgttgg      780
agtgacggca gttatctgga agatcaggat atgtggcgga tgagcggcat tttccgtgac      840
gtctcgttgc tgcataaacc gactacacaa atcagcgatt ccatgttgc cactcgcttt      900 aatgatgatt tcagccgcgc tgtactggag gctgaagttc agatgtgcgg cgagttgcgt      960
gactacctac gggtaacagt ttctttatgg cagggtgaaa cgcaggtcgc cagcggcacc     1020
gcgcctttcg gcggtgaaat tatcgatgag cgtggtggtt atgccgatcg cgtcacacta     1080
cgtctgaacg tcgaaaaccc gaaactgtgg agcgccgaaa tcccgaatct ctatcgtgcg     1140
gtggttgaac tgcacaccgc cgacggcacg ctgattgaag cagaagcctg cgatgtcggt     1200
ttccgcgagg tgcggattga aaatggtctg ctgctgctga acggcaagcc gttgctgatt     1260
cgaggcgtta accgtcacga gcatcatcct ctgcatggtc aggtcatgga tgagcagacg     1320
atggtgcagg atatcctgct gatgaagcag aacaacttta acgccgtgcg ctgttcgcat     1380
tatccgaacc atccgctgtg gtacacgctg tgcgaccgct acggcctgta tgtggtggat     1440
gaagccaata ttgaaaccca cggcatggtg ccaatgaatc gtctgaccga tgatccgcgc     1500
tggctaccgg cgatgagcga acgcgtaacg cgaatggtgc agcgcgatcg taatcacccg     1560
agtgtgatca tctggtcgct ggggaatgaa tcaggccacg gcgctaatca cgacgcgctg     1620
tatcgctgga tcaaatctgt cgatcccttcc cgcccggtgc agtatgaagg cggcggagcc     1680
gacaccacgg ccaccgatat tatttgcccg atgtacgcgc gcgtggatga agaccagccc     1740
ttcccggctg tgccgaaatg gtccatcaaa aaatggcttt cgctacctgg agagacgcgc     1800
ccgctgatcc tttgcgaata cgcccacgcg atgggtaaca gtcttggcgg tttcgctaaa     1860
tactggcagg cgtttcgtca gtatccccgt ttacagggcg gcttcgtctg ggactgggtg     1920
gatcagtcgc tgattaaata tgatgaaaac ggcaacccgt ggtcggctta cggcggtgat     1980
tttggcgata cgccgaacga tcgccagttc tgtatgaacg gtctggtctt tgccgaccgc     2040
acgccgcatc cagcgctgac ggaagcaaaa caccagcagc agttttttcca gttccgtttta    2100 tccgggcaaa ccatcgaagt gaccagcgaa tacctgttcc gtcatagcga taacgagctc     2160
ctgcactgga tggtggcgct ggatggtaag ccgctggcaa gcggtgaagt gcctctggat     2220
gtcgctccac aaggtaaaca gttgattgaa ctgcctgaac taccgcagcc ggagagcgcc     2280
gggcaactct ggctcacagt acgcgtagtg caaccgaacg cgaccgcatg gtcagaagcc     2340
gggcacatca gcgcctggca gcagtggcgt ctggcgaaaa acctcagtgt gacgctcccc     2400
gccgcgtccc acgccatccc gcatctgacc accagcgaaa tggattttttg catcgagctg     2460 ggtaataagc gttggcaatt taaccgccag tcaggctttc tttcacagat gtggattggc     2520
gataaaaaac aactgctgac gccgctgcgc gatcagttca cccgtgcacc gctggataac     2580
gacattggcg taagtgaagc gacccgcatt gaccctaacg cctgggtcga acgctggaag     2640
gcggcgggcc attaccaggc cgaagcagcg ttgttgcagt gcacggcaga tacacttgct     2700
```

```
gatgcggtgc tgattacgac cgctcacgcg tggcagcatc aggggaaaac cttatttatc     2760
agccggaaaa cctaccggat tgatggtagt ggtcaaatgg cgattaccgt tgatgttgaa     2820
gtggcgagcg ataccgcca tccggcgcgg attggcctga actgccagct ggcgcaggta     2880
gcagagcggg taaactggct cggattaggg ccgcaagaaa actatcccga ccgccttact     2940
gccgcctgtt ttgaccgctg ggatctgcca ttgtcagaca tgtataccc gtacgtcttc     3000 ccgagcgaaa acggtctgcg ctgcgggacg cgcgaattga attatggccc acaccagtgg     3060
cgcggcgact ccagttcaa catcagccgc tacagtcaac agcaactgat ggaaaccagc     3120
catcgccatc tgctgcacgc ggaagaaggc acatggctga atatcgacgg tttccatatg     3180
gggattggtg cgacgactc ctggagcccg tcagtatcgg cggaattcca gctgagcgcc     3240
ggtcgctacc attaccagtt ggtctggtgt caaaaataa                            3279

<210> SEQ ID NO 2
<211> LENGTH: 131
<212> TYPE: DNA
<213> ORGANISM: Human immunodeficiency virus type 1

<400> SEQUENCE: 2
ctctcgacgc aggactcggc ttgctgaagc gcgcacagca agaggcgagg ggcggcgact     60
ggtgagtacg ccaattttg actagcggag gctagaagga gagagatg ggtgcgagag        120 cgtcggtatt a                                                          131

<210> SEQ ID NO 3
<211> LENGTH: 84
<212> TYPE: DNA
<213> ORGANISM: Human immunodeficiency virus type 1

<400> SEQUENCE: 3
ctctcgacgc aggactcggc ttgctgaagc gcgcacagca agaggcgagg ggcggcgact     60
ggtgagtacg ccaattttg acta                                             84

<210> SEQ ID NO 4
<211> LENGTH: 67
<212> TYPE: DNA
<213> ORGANISM: Human immunodeficiency virus type 1

<400> SEQUENCE: 4
agcaagaggc gagggcggc gactggtgag tacgccaatt tttgactagc ggaggctaga      60
aggagag                                                               67

<210> SEQ ID NO 5
<211> LENGTH: 88
<212> TYPE: DNA
<213> ORGANISM: Human immunodeficiency virus type 1

<400> SEQUENCE: 5
agcaagaggc gagggcggc gactggtgag tacgccaatt tttgactagc ggaggctaga      60
aggagagaga gacgggtgcg agagcgtc                                        88

<210> SEQ ID NO 6
<211> LENGTH: 31
<212> TYPE: DNA
<213> ORGANISM: Artificial Sequence
<220> FEATURE:
<223> OTHER INFORMATION: primer for amplifying SL23 and SL234 sequences
      of Human immunodeficiency virus type 1
```

-continued

```
<400> SEQUENCE: 6
gggggtgacc tttaaaagca agaggcgagg g                                   31

<210> SEQ ID NO 7
<211> LENGTH: 28
<212> TYPE: DNA
<213> ORGANISM: Artificial Sequence
<220> FEATURE:
<223> OTHER INFORMATION: primer for amplifying SL23 sequence of Human
      immunodeficiency virus type 1

<400> SEQUENCE: 7
gggggtgacc ctctccttct agcctccg                                       28

<210> SEQ ID NO 8
<211> LENGTH: 31
<212> TYPE: DNA
<213> ORGANISM: Artificial Sequence
<220> FEATURE:
<223> OTHER INFORMATION: primer for amplifying SL234 sequence of Human
      immunodeficiency virus type 1

<400> SEQUENCE: 8
gggggtgacc gacgctctcg cacccgtctc t                                   31
```